United States Patent [19]
Muller

[11] Patent Number: 6,063,072
[45] Date of Patent: *May 16, 2000

[54] METHODS AND SYSTEMS FOR CORRECTION OF HYPEROPIA AND/OR ASTIGMATISM USING ABLATIVE RADIATION

[75] Inventor: David F. Muller, Boston, Mass.

[73] Assignee: Summit Technology, Inc., Waltham, Mass.

[ * ] Notice: This patent is subject to a terminal disclaimer.

[21] Appl. No.: 08/818,948

[22] Filed: Mar. 17, 1997

Related U.S. Application Data

[63] Continuation-in-part of application No. 08/351,826, Dec. 8, 1994, Pat. No. 5,613,965.

[51] Int. Cl.[7] .................................................. A61N 5/06
[52] U.S. Cl. ................................. 606/5; 606/10; 606/13; 606/17
[58] Field of Search ........................... 606/2, 3, 5, 10–13, 606/17, 18

[56] References Cited

U.S. PATENT DOCUMENTS

| | | |
|---|---|---|
| 3,980,399 | 9/1976 | Howden . |
| 4,185,897 | 1/1980 | Frieder . |
| 4,724,522 | 2/1988 | Belgorod . |
| 4,729,372 | 3/1988 | L'Esperance, Jr. . |
| 4,856,513 | 8/1989 | Muller . |
| 4,887,592 | 12/1989 | Loertscher . |
| 4,941,093 | 7/1990 | Marshall et al. . |
| 4,973,330 | 11/1990 | Azema et al. . |
| 4,994,058 | 2/1991 | Raven et al. . |
| 5,019,074 | 5/1991 | Muller . |
| 5,152,759 | 10/1992 | Parel et al. . |
| 5,256,853 | 10/1993 | McIntyre . |
| 5,281,211 | 1/1994 | Parel et al. . |
| 5,613,965 | 3/1997 | Muller .................................................. 606/5 |

FOREIGN PATENT DOCUMENTS

| | | |
|---|---|---|
| 1 210 128 | 8/1986 | Canada . |
| 0 346 116 | 12/1989 | European Pat. Off. . |
| 0 467 775 | 1/1992 | European Pat. Off. . |
| 0 525 902 | 7/1992 | European Pat. Off. . |
| 42 19 809 | 12/1993 | Germany . |
| WO 91/04829 | 4/1991 | WIPO . |
| WO 93/25166 | 12/1993 | WIPO . |
| WO 96/17566 | 6/1996 | WIPO . |

OTHER PUBLICATIONS

Rioux, M. et al., "Linear, annular, and radial focusing with axicons and applications to laser machining", *Applied Optics*, vol. 17 (10), pp. 1532–1536.

*Primary Examiner*—David M. Shay
*Attorney, Agent, or Firm*—Thomas J. Engellenner; Nutter, McClennen & Fish, LLP

[57] ABSTRACT

Methods and apparatus for corneal reprofiling are disclosed in which a beam-swapping assembly is employed to redirect rays of ablative radiation passing through the assembly. Essentially, the beam-swapping assembly turns the beam profile "inside out" redirecting the inner most rays to the periphery of the beam while redirecting the outer rays at the same time to the center of the beam. The beam-swapping assembly can be used in conjunction with a beam-shaper, such as an adjustable iris or other beam-shaping device, to create convoluted annular ablation patterns of variable depth and, thereby, perform hyperopia and/or astigmatism correcting procedures.

18 Claims, 4 Drawing Sheets

METHODS AND SYSTEMS FOR CORRECTION OF HYPEROPIA AND/OR ASTIGMATISM USING ABLATIVE RADIATION

RELATED APPLICATIONS

This application is a continuation-in-part of the commonly-owned U.S. patent application Ser. No. 08/351,826, filed on Dec. 8, 1994, now U.S. Pat. No. 5,613,965 herein incorporated by reference.

BACKGROUND OF THE INVENTION

The technical field of this invention is corneal surgery and, in particular, the invention relates to methods and systems for correction of hyperopia and/or astigmatism using ablative radiation.

Recently, it has been demonstrated that changes in the refractive power of the eye can be achieved by laser ablation of the corneal surface. Such procedures, known as photorefractive keratectomy, involves the use of a nonthermal, high energy, laser radiation to sculpt the cornea into an ideal shape. For details, see, Marshall et al. "Photoablative Reprofiling of the Cornea using an Excimer Laser: Photorefractive Keratectomy," Vol. 1, Lasers in Ophthalmology, pp. 21–48 (1986); and Tuft et al. "Stromal Remodeling Following Photorefractive Keratectomy," Vol. 1, Lasers in Ophthalmology, pp. 177–183 (1987), herein incorporated by reference.

The cornea of the eye comprises transparent avascular tissue. The cornea functions as both a protective, anterior membrane and a "window" through which light passes as it proceeds to the retina. The cornea is composed of a set of distinct layers: the outer epithelium, an anterior elastic lamina known as "Bowman's membrane," the cornea proper (or "stroma"), a posterior elastic lamina known as "Descemet's membrane", and the inner endothelium. The stroma is fibrous and constitutes the major portion of the cornea. Bowman's membrane, which forms the outer elastic lamina, is a rigid fibrillar structure not tending to cut or fracture, while Descemet's membrane, which forms the inner elastic lamina, is very brittle but elastic and has a tendency to curl. Together, the Bowman's and Descemet's membranes impart the necessary curvature to the stromal tissue. This curvature of the cornea constitutes an major component of the refractive power of the eye, thereby allowing objects to be imaged onto the retina.

The average adult cornea is about 0.65 mm thick at the periphery, and about 0.54 mm thick in the center. Photorefractive keratectomy involves sculpting the uppermost regions of the cornea, namely, the epithelium, Bowman's membrane, and the outer stroma. The epithelium consists of five or six layers of cells, and the underlying Bowman's membrane, is also a very thin structure. The corneal stroma accounts for about 90 percent of the corneal thickness. In performing photorefractive keratectomy operations on the cornea, care must be taken to avoid damaging the underlying Descemet's membrane or endothelium.

In photorefractive keratectomies, a laser photoablation apparatus is used to change the curvature of the cornea, at least in the so-called "optical zone" or region of the cornea through which light must pass to enter the pupil and reach the retina. The size of the optical zone will, of course, vary from individual to individual, and will also vary based upon ambient light conditions (because the pupil will dilate and contract in response to ambient light). The extent of the sculpted region (and the depth of ablation) will depend on the amount of correction needed to achieve optimal vision. For example, correction of relatively mild myopia (nearsightedness) on the order of 2 Diopters requires only a modest flattening of the corneal curvature, which can be accomplished in a region of small cross-sectional area (e.g., affecting a circular region of the cornea in front of the pupil less than 5 millimeters in diameter). However, when more complicated refractive errors, such as more severe myopia, hyperopia (farsightedness) or astigmatisms, are corrected by photorefractive keratectomy procedures, the sculpted area will extend across a much larger portion of the cornea, e.g., affecting a region as large as 8 mm in diameter or more.

One approach to performing photorefractive keratectomy procedures is to employ an optical system which varies the size of the exposed surface area to which the laser radiation is applied. In one embodiment of such a "variable exposure area" system, a beam-shaping stop or window is moved axially along the beam to increase or decrease the region of cornea on which the laser radiation is incident. Alternatively, an adjustable iris can be deposed in the beam path. In either approach, by progressively varying the size of the exposed region, a desired photoablation profile is established on the surface. For further details on these techniques see U.S. Pat. No. 4,973,330 issued to Azema et al. on Nov. 27, 1990; and U.S. Pat. No. 4,941,093 issued to Marshall et al. on Jul. 10, 1990, herein incorporated by reference.

Another technique for corneal reshaping involves the use of a beam-shaping mask which is disposed between the laser and the surface. The mask provides a predefined profile of resistance to erosion by laser radiation selectively absorbing some of the laser radiation while permitting the remainder to be transmitted to the surface in accordance with the mask profile. For further disclosures of such masking techniques, see U.S. Pat. No. 4,856,513 issued to Muller on Aug., 15, 1989; U.S. Pat. No. 4,994,058 issued to Raven et al. on Feb. 19, 1991; U.S. Pat. No. 5,019,074 issued to Muller on May 28, 1991, and U.S. Pat. No. 5,324,281, issued to Muller on Jun. 28, 1994, all of which are incorporated herein by reference.

To correct hyperopia, in particular, it is necessary to increase (steepen) the curvature of the cornea. Hyperopia correction, which can require significant sculpting in a ring-like region having a diameter of about 4 mm to 8 mm, places additional demands on the engineering design of a photorefractive keratectomy apparatus, which normally must be met by increasing the size and/or power of the laser source. Increasing the power of the laser to compensate for inefficiencies in beam delivery is undesirable because large annular beams deliver a larger total amount of energy to the cornea per pulse.

Moreover, in performing hyperopia and/or astigmatic corrections, it is also often desirable to create a "blend zone" at the periphery of the sculpted region. Such blend zones provide an edge-smoothing effect where there would otherwise be a sharp circular (or elliptical) recess of a depth proportional to the magnitude of dioptric correction. Because sharp edges tend to induce regression of the reprofiled curvature, a blend zone provides an outer, profile-smoothing, region contiguous with the curvature-corrected zone. However, this blend zone further taxes the photorefractive keratectomy apparatus because the zone must be created, at least in part, beyond the outer edge of the sculpted region and therefore can extend the overall diameter of the reprofiled region to as large as 10 millimeters.

In addition, the formation of a blend zone at the outer periphery of the reprofiled cornea typically requires a reverse procedure, at least when a movable stop is employed, to perform hyperopia and/or astigmatic corrections. A different type of stop may be used to deliver an annular pattern of radiation of progressively decreasing intensity to the outermost portions of the blend zone. This second stage in the procedure typically doubles the overall time that a patient must remain motionless with his or her eye aligned with the apparatus.

There exists a need for a better photorefractive keratectomy apparatus for refractive correction of hyperopia and/or astigmatism, as well as creation of blend zones, without resort to larger lasers. There also exists a need for systems that can achieve desired blend zones at the periphery of hyperopic or astigmatic correction regions with less waste of laser energy. In addition, a photorefractive keratectomy system that could facilitate simplified and/or quicker formation of peripheral blend zones would satisfy a long-felt need in the art.

SUMMARY OF THE INVENTION

Methods and apparatus for corneal reprofiling are disclosed in which a beam-swapping assembly is employed to redirect rays of ablative radiation passing through the assembly. Essentially, the beam-swapping assembly turns the beam profile "inside out" redirecting the inner most rays to the periphery of the beam while redirecting the outer rays at the same time to the center of the beam. The beam-swapping assembly can be used in conjunction with a beam-shaper, such as an adjustable iris or other beam-shaping device, to create convoluted annular ablation patterns of variable depth and, thereby, perform hyperopia and/or astigmatism correcting procedures.

The systems and methods of the present invention are more generally useful in any corneal reprofiling procedures which involve applying convoluted annular patterns of ablative radiation onto the cornea. Such annular beams can be applied not only to provide hyperopia and/or astigmatism correction but also to create "blend zones" thereby reducing any surface discontinuities on the cornea associated with the correction procedures.

The present invention permits ablation of the peripheral portions of the cornea in broad annular patterns without wasting a major component of the beam, and without resort to larger or more powerful lasers. The term "peripheral region" or "periphery" as used herein with reference to the cornea is intended to describe that portion of the cornea which forms the boundary between the reprofiled central region of the cornea and the surrounding unablated region. As such, it encompasses the unablated or minimally ablated regions adjacent to the central portion, or optical zone, where photorefractive keratectomy is performed.

Preferably, the systems and methods of the present invention also involve changing the intensity distribution of the light beam, such that the annulus of radiation has a varying intensity as a function of radius and, thereby, achieves a blending effect with the least number of pulses.

As used herein, the terms "annular" and "annulus" are used to denote ring-like patterns of radiation of generally circular, elliptical or oval shape.

As used herein, the term "convoluted beam" is intended to describe an ablative beam in which the rays of the inner segments of the beam, i.e., at a relatively smaller distance from the optical axis, have been re-directed towards the periphery of a resulting beam, and in which the rays of the outer segments of the beam have been re-directed at the same time towards the center of the beam.

As used herein, the term "variable intensity" is intended to encompass beams of radiation that vary in energy or fluency across their cross-section. For example, in the case of an annular beam, the intensity can vary radially from a higher relative intensity (and, hence, ablative power) at an inner segment of the ring to a lower intensity at the outer or peripheral segment of the annulus.

Variations in ablative power of the annular beam of the present invention need not be linear or even unidirectional (e.g. progressively increasing or decreasing). In one embodiment, a non-linear variable intensity annulus of ablative radiation is disclosed which is particularly useful in creating the "blend zone" at the periphery of the optical zone of the cornea during a hyperopia correcting procedure. In this embodiment, the intensity of the ablative radiation is ideally low or close to zero at the inner segment of the annulus but rapidly increases to a peak value and then progressively tapers off at the outer edge of the ablative ring.

Other variations in intensity profile can be employed by those skilled in the art for particular applications. For example, the shape of the intensity profile can be further modified to complement the basic reprofiling procedure, such that the selected intensity profile and the ablation procedure achieve a cumulative effect that results in a smooth profile. Thus, the annular intensity profile itself might not achieve a smooth transition if applied alone to the cornea, but instead provides a second order effect which, when combined with the sculpting action of the corrective ablation operations, achieves a desired blending effect in the boundary region between the reprofiled region and the unablated peripheral cornea.

Accordingly, in one aspect of the invention, a photorefractive keratectomy system for reprofiling a cornea of a patient is disclosed including a radiation source for emitting a beam of ablative radiation. The system also includes a beam-shaper for receiving the beam and for varying its cross-sectional size or otherwise selectively transmitting at least a portion of the beam. The system further includes a beam-swapping assembly for modifying at least a portion of the beam passing through the beam-shaper to create a convoluted annular beam of radiation having an intensity profile which varies radially within the annulus of the beam.

The beam-swapping assembly applies the annular beam to the cornea to remove a selected volume of corneal tissue from a region in an optical zone of the cornea with the ablative radiation, thereby forming a reprofiled region which steepens, at least in part, a curvature of the cornea.

In one embodiment of the invention, the beam-swapping assembly includes a lens element having a front face and a rear face, the front face being conical such that a light beam incident on the front face along the optical axis will be refracted into an annular beam. In another embodiment, the front face of the lens element of the beam-swapping assembly has a non-linear surface for varying the intensity profile of the annular beam. In still another embodiment of the invention, the rear face of the lens element of the beam-swapping assembly has a non-linear surface of varying the intensity profile of the annular beam.

In another aspect of the invention, a class of optical elements are disclosed which can be used to generate the annular beams of the present invention. Such optical elements have a predetermined index of refraction, a first surface for receiving light and a second surface from which light exits, the optical element refracting a light beam incident along an optical axis into a annular beam having an intensity that varies radially within the annulus of the beam.

In particular, lens elements are disclosed having a generally conic front face and a rear face which is generally perpendicular to the path of the incident beam. Light passing through this optical element will be refracted into an annular beam. Variations in the intensity profile of the annular beam can be introduced by employing an initial beam which has a non-uniform profile, or by modifying the shape of either the front face or the rear face of the optical element. For example, by using an appropriately design conical front face and introducing a slight convex curve to the rear face, an annular beam having a progressively decreasing intensity (from inner to outer ring segments) can be obtained. The optical elements of the present invention can also be designed to provide a convoluted annular beam.

In yet another aspect of the invention, a method of photokeratectomy for correction of a cornea of an eye of a patient is disclosed. The method includes the steps of providing a beam of ablative radiation; and varying a cross-sectional size of at least a portion of the beam by passing the beam through an adjustable beam shaper.

Although the invention is largely described in conjunction with an adjustable iris beam shaper, such as an adjustable iris, which provides a beam having a cross-sectional opening which varies over time, various other beam-shaping devices can be used to effect changes in the depth of corneal ablation. For example, a succession of different apertures (e.g., on a wheel or moving band) can be presented in the beam path to change the beam dimensions. Analogous results can be obtained with a succession of mirrors of different sizes. Moreover, graded intensity masks, erodable masks and rotating beam modulators can likewise be employed to selectively transmit portions of the beam. To create astigmatic ablation profiles, the succession of apertures or mirrored surfaces can be elliptical in shape, the masking element can be astigmatic, the beam-shaper can be tilted, or a cylindrical lens can be added. Alternatively, the astigmatic component of the ablative profile can be achieved by an aspheric beam-swapping assembly.

The method of the invention can further include the steps of modifying the beam received from the adjustable beam shaper into a convoluted annular beam having an intensity profile which varies within the annulus of the beam; and applying the convoluted annular beam to the cornea to remove a selected volume of corneal tissue from a region of an optical zone of the cornea, thereby forming a reprofiled region which steepens, at least in part, a curvature of the cornea.

In an embodiment, the step of applying the convoluted annular beam can further include applying the beam to create a blend zone in a peripheral region of the optical zone of the cornea, thereby permitting smooth transition between the reprofiled region and an unablated region of the cornea In other embodiments, the step of modifying the beam can include modifying the beam into a convoluted annular beam having, at least in part, a radially increasing intensity profile, a radially decreasing intensity profile, and/or an intensity profile which first increases and then decreases as a function of radial distance from an axis.

In another embodiment, the step of modifying the beam can include modifying the beam into a convoluted beam having an intensity profile which varies radially within the annulus of the beam in such a way as to compliment the forming of a reprofiled region in the optical zone of the cornea and the creation of a blend zone in the peripheral region of the optical zone of the cornea.

The invention will next be described in connection with certain illustrated embodiments; however, it should be clear that those skilled in the art can make various modifications, additions and subtractions without departing from the spirit or scope of the invention. It should also be noted that the invention can be used for procedures other than simply corneal reprofiling. For example, the present invention can be practiced in connection with corneal transplants where a donor button is inserted into the patient's eye. As part of such a procedure, the transplanted cornea can be reprofiled and then a blend zone created to smooth any discontinuities resulting from either the reprofiling or the juncture of the donor button and the corneal transplant bed.

In addition, the present invention can be used in the course of laser-assisted, in situ keratoplasty (also known as "LASIK" procedures) where a portion of the cornea (e.g., the epithelium, Bowman's membrane and the outermost layers of the stroma) is removed, a reprofiling procedure is then performed in the exposed stroma, and the excised layer is then reattached to the reprofiled surface of the corneal stroma. In this approach, the annular exposure beam can be used effectively to ensure that the reprofiled stromal tissue does not have boundary effects that would prohibit re-attachment of the excised cap structure.

BRIEF DESCRIPTION OF THE DRAWINGS

The invention will now be described by way of example with reference to the accompanying drawings, like reference characters on the drawings indicating like parts in several figures, in which.

DETAILED DESCRIPTION

The present invention for systems and methods for photorefractive keratectomy can be used to provide an overall reprofiling of the corneal surface for hyperopia and astigmatism. In general, hyperopic conditions can be corrected by imparting a steeper curvature to the cornea overall. This can be achieved, for example, by exposing the optical zone generally (i.e., the central region of the cornea, approximately 2 millimeters to about 7 millimeters in diameter) to a succession of pulses of light energy while controlling the area exposed by each pulse, so as to successively change the exposure area.

When an increase in convexity is required (e.g., to correct hyperopia), the peripheral regions are exposed to a greater extent than the central region, thereby leaving a "bulge" in the middle of the cornea by selective application of laser energy. In the practice of the present invention, hyperopia can be corrected by reprofiling the cornea to provide normal visual acuity over most of the optical zone. However, at the edge of the reprofiled region, a rim-like discontinuity will be created in the corneal surface.

Similar composite profiles can be achieved for correction of astigmatism. To achieve a correction of astigmatism, the ablative radiation can be applied in an elliptical pattern to preferentially steepen the curvature along the minor. (Alternatively, the ablative radiation is selectively applied to the eye, in accordance with the astigmatic axis to preferentially flatten the curvature along the axis where the astigmatic bulge is present.)

The source of ablative radiation can be is designed so as to produce pulses of light having substantially constant energy density, such that a known depth of surface material will be eroded for each pulse. By using relatively low power, only a microscopically thin layer of material will be removed in response to each pulse. By continual monitoring and feedback, a very accurate profiling of the cornea can be achieved.

In order to locate the eye relative to the laser means, conventional suction rings or cups may be used, such as those provided by Steinway Instruments of San Diego, Calif., USA. Alternatively, modified vacuum-fixed stages can be used. In either event, the fixation means is typically applied to the white (sclera) region of the eye and connected to a low suction pressure sufficient to clamp the cup or stage to the eye but not so great that the cornea is distorted. The cup or stage may then be fixed to further apparatus (in the present case, this will normally be the optical system of the laser) which will thereby be located accurately with respect to the eye.

Alternatively, the patient can be asked to look at a fixation light source which transmits a fixation light ray to the eye along a path that is essentially collinear with the ablation beam. The clinician can monitor the patient to ensure that the eye is fixed on the fixation light source, thereby allowing the beam to be transmitted to the eye along the visual axis which is essentially coincident with the optical axis (corneal apex) of the eye.

Excimer lasers and halogen lasers operating to generate UV radiation are presently preferred for corneal ablation and, in particular, argon-fluoride (ArF) excimer lasers operation at about 193 nm are preferred. In medical uses such as corneal ablation, it is preferred to use an excimer laser which is designed for medical applications. (Other lasers such as HF, pulsed $CO_2$, infrared lasers at wavelengths of about 2.6–3.1 μm, Er:YSGG and Er:YAG lasers may also be used.) In most instances, a laser which generates a low divergence beam is desirable. Low divergence can be achieved, for example, by incorporating an astable resonator into the laser cavity.

The pulse repetition rate for the laser may be chosen to meet the needs of each particular application. Normally the rate will be between 1 and 500 pulses per second, preferably between 1 and 100 pulses per second. When it is desired to vary the beam size, the laser pulses may be stopped. Alternatively, the beam size may be varied while the pulses continue. If a measurement device is used to monitor the erosion progress and control the laser system automatically, the beam size may be varied continuously at a controlled rate without interrupting the pulses.

Suitable irradiation intensities vary depending on the wavelength of the laser and the nature of the irradiated object. For any given wavelength of laser energy applied to any given material, there typically will be a threshold value of energy density below which significant erosion does not occur. Above the threshold density, there will be a range of energy densities over which increasing energy densities give increasing depths of erosion, until a saturation value is reached. For increases in energy density above the saturation value, no significant increase in erosion occurs.

The threshold value and the saturation value can vary from wavelength to wavelength of laser energy and from one layer of the cornea to another layer. However, for any particular laser and any particular material, the values can be found readily by experiment.

For example, in the case of eroding Bowman's membrane and stromal portions of the cornea by energy of wavelength 193 nm (the wavelength obtained from an ArF Excimer laser), the threshold value is about 40 mJ per $cm^2$ per pulse, and the saturation value is about 250 mJ per $cm^2$ per pulse. There appears to be little benefit in exceeding the saturation value by more than a small factor, and suitable energy densities at the corneal surface are 50 mJ per $cm^2$ to one J per $cm^2$ per pulse for a wavelength of 193 nm.

The threshold value can vary very rapidly with wavelength, and at 157 nm, which is the wavelength obtained from an $F_2$ laser, the threshold is about 5 mJ per $cm^2$ per pulse. At this wavelength, suitable energy densities at the corneal surface are 5 mJ per $cm^2$ to one J per $cm^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per $cm^2$ per pulse), it is preferable to provide to the cornea pulses of an energy density of 90 to 220 mJ per $cm^2$ per pulse. Typically, a single pulse will erode a depth in the range of about 0.1 to 1 micrometer of collagen from the cornea.

In one clinical procedure, for example, a laser system capable of measurement and reprofiling to create a region of greater curvature for correction of hyperopia includes one of the above-described laser sources, a beam-shaper, such an iris, a beam-swapping assembly, and a control unit. A surgical microscope can be employed to allow the surgeon to aim the laser correctly. After initial setting up and alignment using the microscope , reprofiling is effected by appropriate operative signals from the control unit.

Reprofiling of the cornea can be achieved by varying the shape and size of the ablative radiation beam so that different regions of the cornea receive different numbers of pulses and are, therefore, eroded to a different extent. Since the normal surface of a cornea is convex, the effect of a concave ablation profile effectively will be to flatten the surface of the cornea slightly. Flattening the surface of the cornea serves to decrease the refractive power of the eye. Conversely, increasing the curvature of the cornea by effecting a convex erosion pattern, increases the refractive power of the eye.

Figure 1:
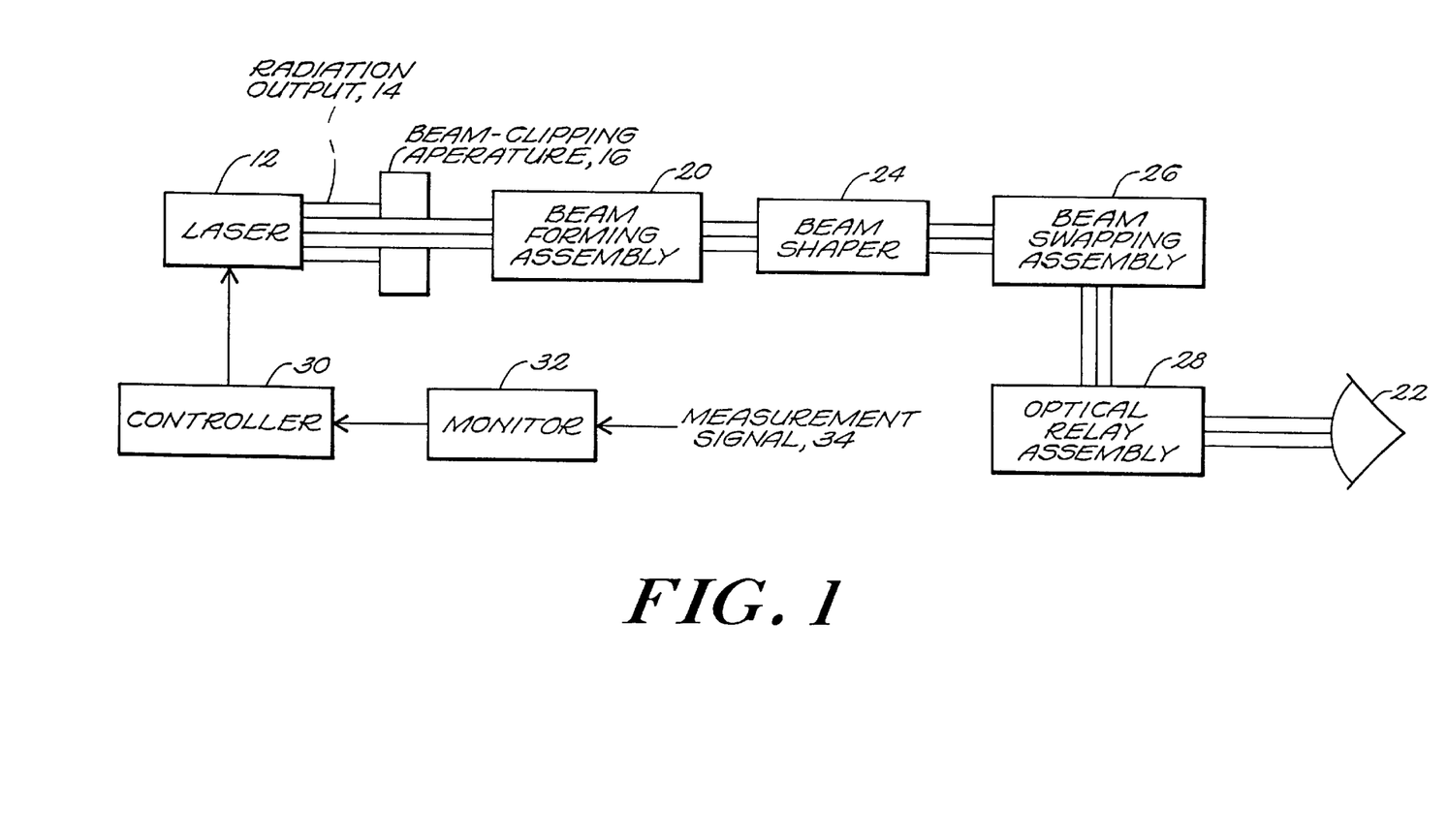
FIG. 1 is a schematic illustration of an apparatus for reprofiling the surface of a cornea in accordance with the present invention.

In FIG. 1, a system for performing photorefractive keratectomy is shown, including a laser 12 which provides a radiation output 14. The system 10 can also include an initial beam-clipping aperture 16. The system 10 can also include a beam-forming assembly 20 which preferably operates to produce a collimated beam of uniform cross-section and low divergence. (Beam-forming systems including anamorphic lens assemblies are disclosed in U.S. Pat. No. 4,941,093, herein incorporated by reference.) The system 10 further includes a beam-shaper 24, such as an iris, for varying the size of the ablative beam or otherwise selectively transmitting portions of the ablative beam, and a beam-swapping assembly 26, for generating a convoluted beam of ablative radiation. Optionally, the system 10 further includes an optical relay assembly 28 which serves to either project or image the output of the beam-swapping assembly 26 onto the surface of a cornea 22.

The laser 12 can be powered and controlled by controller/power supply 30, which can be adjustable to cause the laser to produce pulses of light at a specific frequency and/or intensity. To further control the laser 12, a monitor 32 can be provided which receives measurement signals 34 from the beam-swapping assembly 26 and/or the cornea 22 while it is exposed to a radiation by the laser 12. The monitor 32 can generate a control signal which is communicated to the controller 30 for controlling the laser 12 and/or optionally for controlling the beam-swapping assembly 26.

In practice, the system 10 can operate to reprofile the surface of the cornea 22 to correct refractive errors in vision, such as hyperopia or astigmatism. In such procedures, the beam-shaper 24 can vary a cross-sectional size of at least a portion of the ablative beam 14 between a first diameter to a second diameter.

If the ablative beam was then transmitted directly from the beam-shaper 24 to the cornea of the eye, the central region of the eye would receive more pulses and consequently would erode to a greater extent than the surrounding peripheral regions, as the beam-shaper 24 was opened. In the present invention, however, the ablative beam 14 passes through the opening of the beam-shaper 24 is received and modified by the beam-swapping assembly 26. The beam-swapping assembly 26 "swaps" or refracts rays in the outer segments of the ablative radiation beam, i.e., at a relatively large distance from the optical axis, such that they are in inner segments of the annular beam, i.e., at a relatively smaller distance from the optical axis. The beam-swapping assembly 26 also swaps or refracts rays in inner segments of the ablative radiation beam such that they are in outer segments of the annular beam.

In addition, the beam-swapping assembly 26 can modify the ablative radiation beam such that the convoluted annular beam emitted from the assembly has an intensity which varies radially within the annulus of the beam. The inner segment of the annular ring is applied to the cornea to remove a selected volume of corneal tissue from a region in an optical zone of the cornea, thereby forming a reprofiled region which steepens, at least in part, a curvature of the cornea. The tapered outer edge of the annular ring is applied to a peripheral region of the optical zone of the cornea to create a blend zone between the outer edge of the reprofiled region of the cornea and the peripheral unablated corneal surface.

Accordingly, after a period of time, the beam-shaper 24 and the beam-swapping assembly 26 transmit more and/or relatively higher intensity ablative radiation pulses to the outer regions of the optical zone of the cornea. Consequently, the system 10 erodes a greater volume of corneal tissue from the outer regions of the optical zone of the cornea than the central region of the optical zone. Thus, the actual profile of the eroded surface of the cornea can be steepened in a controlled manner, by controlling the number of the pulses transmitted through each setting of the beam-shaper 24 and/or by modifying the intensity profile of the annular beam emitted from the beam-swapping assembly 26. In addition, the creation of a blend zone between the outer edge of the reprofiled region of the cornea and the peripheral unablated corneal surface ensures that a smooth corneal surface is preserved to promote epithelial cell regrowth and to minimize the degree to which healing processes induce regressive refractive changes.

Where differential erosion is to be effected parallel to a line rather than around a point, an astigmatic optical relay assembly 28 can serve to either project or image the output of the beam-shaper 24 and the beam-swapping assembly 26 into an asymmetric ablation profile onto the surface of the cornea 22. Such techniques can be employed on a cornea to correct astigmatism and the like. Alternatively, the beam-shaper 24 can be fitted to form an elliptical beam.

An automatic feedback control system can be provided in which the output from a measuring device for measuring the shape or an optical property of the eye is used to control the delivery of pulses of laser energy. Alternatively, the desired surface profile may be obtained through erosion by a successive approximation technique. In this technique, a measuring device is used to determine the desired change in the profile of the surface. Pulses of laser energy are delivered to the surface so as to bring about slightly less than the desired alteration. The measuring device is used again to determine the correction now needed to reach the desired profile, and further pulses of laser energy are provided accordingly to produce slightly less than the total calculated correction. This process is repeated until the eroded surface acquires the desired profile to a suitable degree of accuracy.

Suitable measurement devices, commonly called keratometers, are known and commercially available. Examples of such devices include the "Photokeratoscope" manufactured by the Sun Contact Lens Company of Kyoto, Japan, and the "Corneascope" manufactured by International Diagnostic Instruments Limited, Broken Arrow, Okla., USA. (See also, Klyce, "Computer Assisted Corneal Topography," Vol. 25, *Invest. Ophthalmol. Vis. Sci.*, p. 1435 (1984) for a comparison of these instruments and a method of using the "Photokeratoscope").

Figure 2:
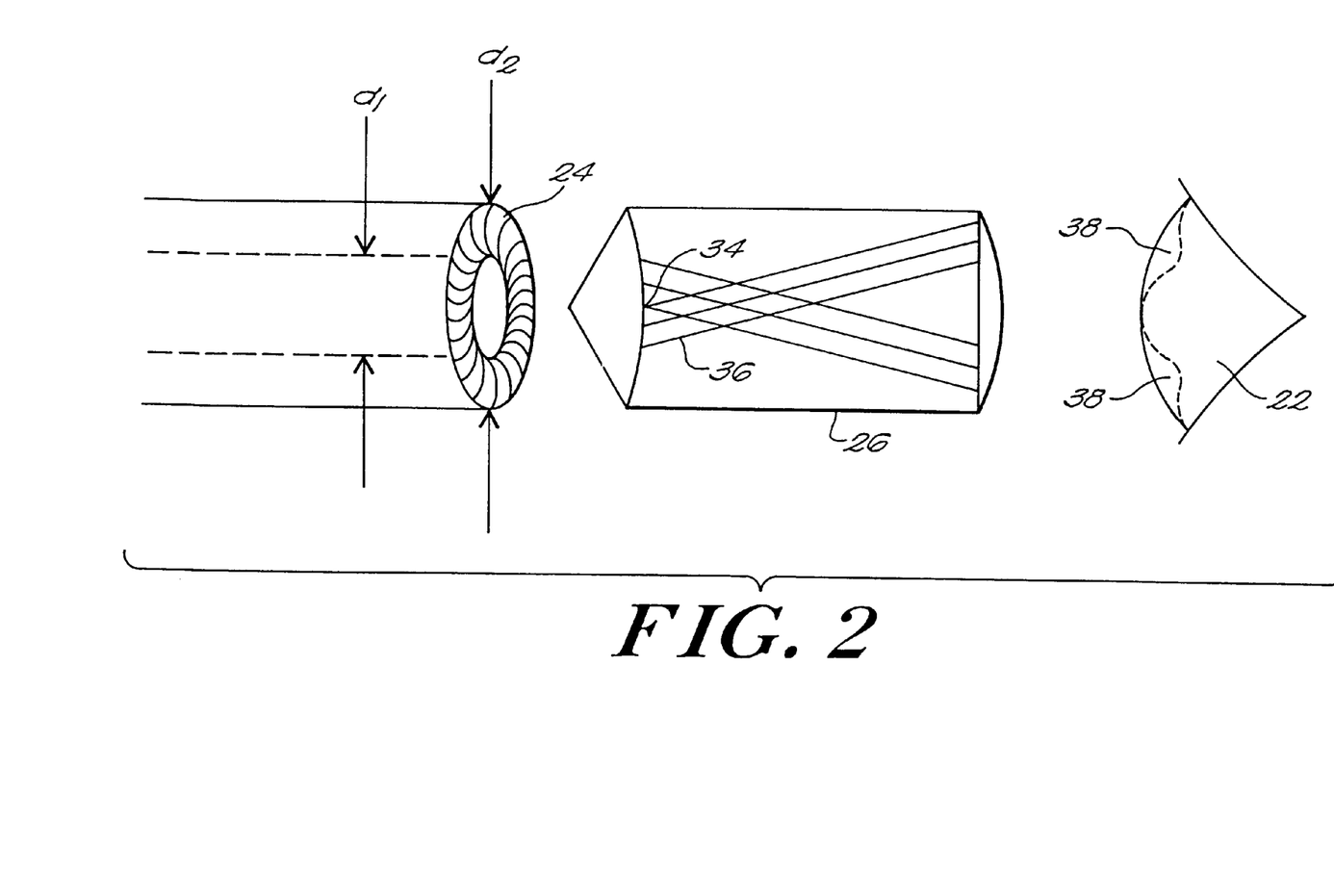
FIG. 2 is a more detailed illustration of a photokeratectomy system and illustrates the functioning of a beam-swapping assembly, in accordance with the present invention.

In FIG. 2, an embodiment of a photorefractive keratectomy system is shown for hyperopic correction. The beam-shaper 24 is shown with an open aperture 35. The beam of ablative radiation is transmitted through the beam-shaper 24 into the beam-swapping assembly 26. Rays in an inner portion 36 of the beam are swapped in the beam-swapping assembly 26 and applied to an outer region of the optical zone 38 of the cornea 22. In practice of the invention, the ablative beam which passes through beam shaper 24 can be varied in size from d1 to d2 over time and a greater number of pulses can be applied to outer regions of the optical zone of the cornea 22.

The beam-shaper 24 and the beam-swapping assembly 26 can operate to create hyperopic correction in a selected portion of the cornea 22 by increasing the curvature of the cornea in this region. A large aperture of the beam-shaper 24 is employed to ablate all (or a substantial portion) of the epithelial layer of the cornea 22 in the selected region of the optical zone so as to expose the surface of Bowman's membrane.

An annular ablation region is then created in Bowman's membrane. A narrower annular ring of further ablation is then created, to create a steepened curvature. Thus, a beam-shaper aperture opening between d1 and d2 is employed to create a ring-like ablation zone which is swapped to the periphery of the optical zone so as to create a "halo-like" profile of ablation, thereby steepening the curvature of the cornea upon regrowth of the epithelial layer over the re-sculpted corneal surface.

It should be clear that some hyperopic (or astigmatic) corrections will require deeper ablation and penetrate into the stroma proper. In some applications, it may be desirable to remove a centicular portion of the cornea (including Bowman's membrane) and perform the entire procedure in the stroma, and then reattach the centicular portion over the reprofiled surface. It should also be clear that the actual procedure is carried out with a substantially greater number of steps than the three steps described above to achieve a smooth curve and minimize the step-effects. Additionally, the order of the steps can be reversed, e.g., by starting with a very narrow peripheral ablation ring and then gradually increasing inwardly the thickness of the annular beam.

Regardless of the technique, however, a surface discontinuity may result. For hyperopic corrections, this surface discontinuity will manifest itself as a rim or groove in the cornea at the boundary between the ablated and unablated regions. For astigmatic corrections, the discontinuity may be an arcuate groove. Upon completion of the laser surgery, the epithelium will attempt to regrow with a uniform thickness over the reprofiled surface. However, when it encounters a surface discontinuity, such as the edge effect, difficulties arise. Either the epithelium is unable to regrow properly or it will tend to fill in the groove with additional layers of cells and thereby reduce the effectiveness of the corneal reprofiling operation.

Figure 3:
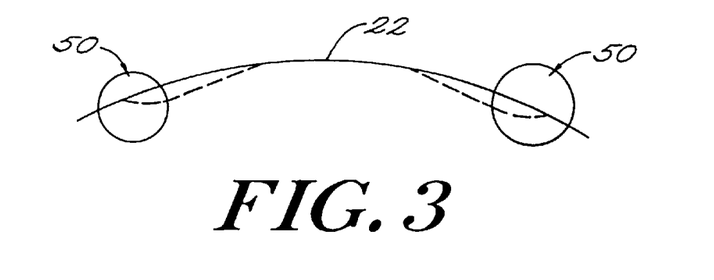
FIG. 3 illustrates the formation of a blend zone according to the present invention to alleviate surface discontinuities.

Therefore, it is desirable to create a blend zone 50 as shown in FIG. 3. The blend zone 50 ensures that the new curvature is maintained within the optical zone while creating a new curve at the periphery that allows a smooth transition to occur between the ablated and unablated regions of the cornea 22.

Figure 4:
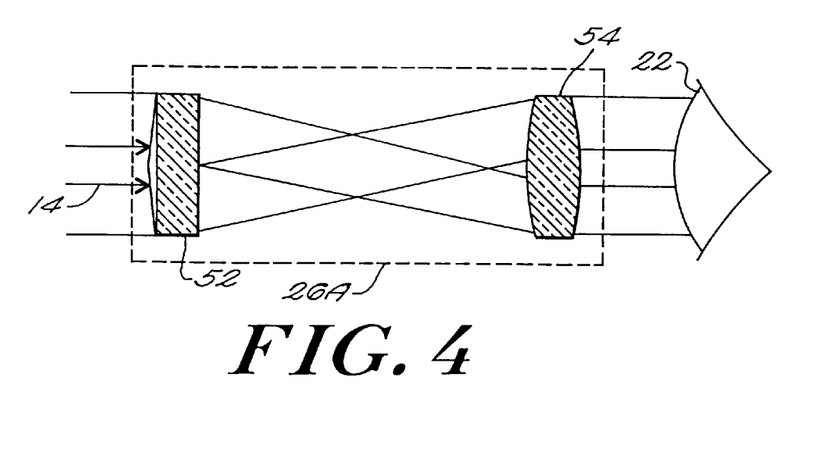
FIG. 4 illustrates a beam-swapping assembly for use in the present invention.

In FIG. 4, another beam-swapping assembly 26A for generating a convoluted annular beam of radiation is shown consisting of a lens element 52 and, optionally, a second collimating lens 54. Lens 52 is designed to convert the input laser radiation 14 into an annular beam. This annular beam is then projected by lens 54 onto the cornea. (It should be clear that various other lens elements can be employed either in place of lens 54 or in addition to lens 54 in order to relay the annular beam to the eye. Such lens systems can either be projection-mode optical systems or imaging systems.)

Figure 5:
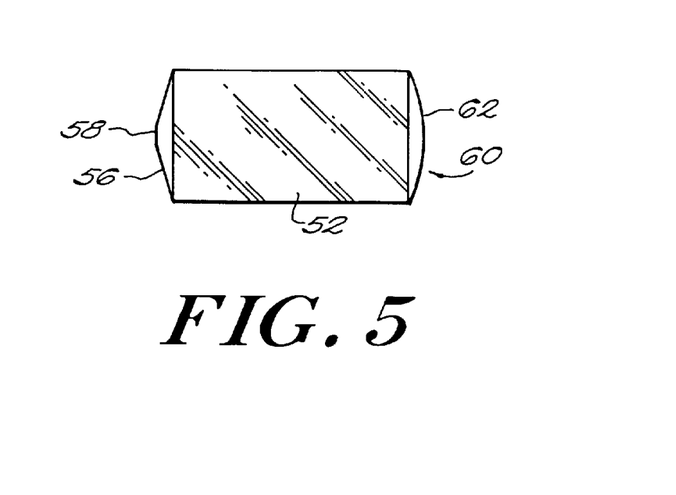
FIG. 5 is an expanded view of the annulus-forming lens of the beam-swapping assembly of FIG. 4 with a roughly 5:1 horizontal scale expansion.

In FIG. 5, the lens element 52 is shown in an expanded shape (with the horizontal dimensions being enlarged in order to illustrate the shape of the front and rear faces of the lens). As shown, the front face of lens 52 includes a conical section 56 and a flat central region 58. The size of this flat central region 58 is variable, depending upon the shape of the annulus desired. In some instances, it may be preferable to treat this flat region central 58 with a reflective coating. The rear face of lens 60 has a slight curved surface 62. In one preferred embodiment, the conical front face 56 and the curved rear face 62, can cooperate to generate a convoluted annulus of radiation and to insure that the radiation intensity profile will vary radially within the annulus of the beam. (Alternatively, lens element 52 can be designed to provide a beam-swapping function with a uniform intensity profile, and, thus, can be useful in more general corneal reshaping systems, e.g., as element 26 in FIG. 2 above.)

Figure 6A:
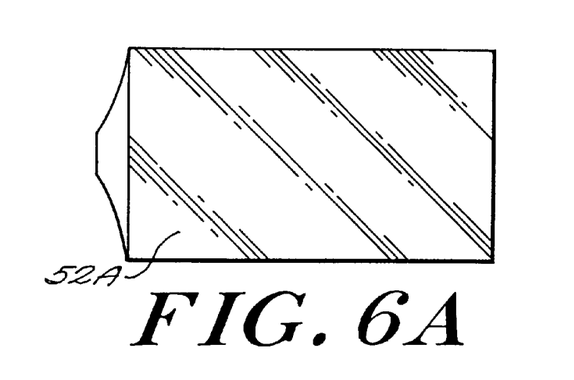
FIG. 6A is an expanded view of a lens element of the beam-swapping assembly useful in producing a convoluted annular beam having a variable intensity profile.
Figure 6B:
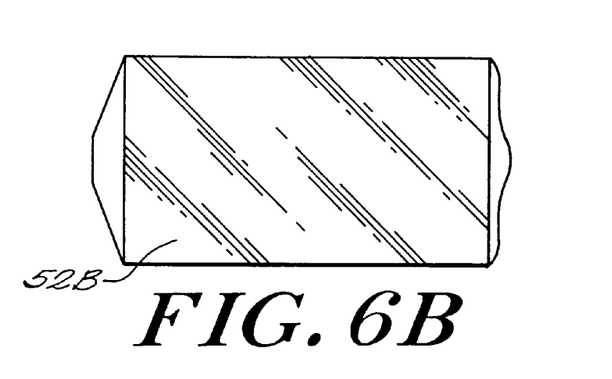
FIG. 6B is an expanded illustration of a lens element of the beam-swapping assembly for producing a variable intensity convoluted annulus of ablative radiation.
Figure 6C:
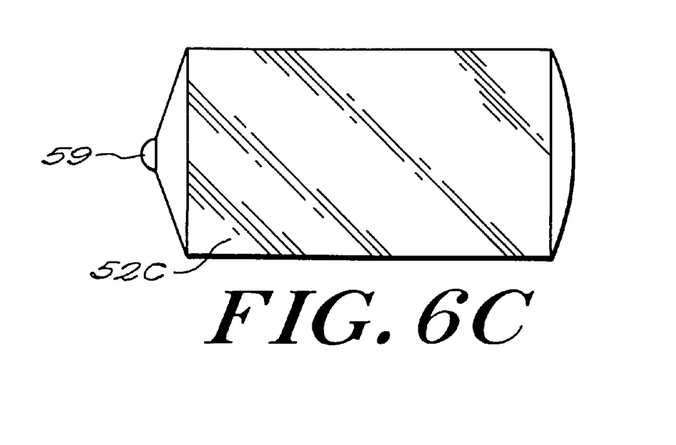
FIG. 6C is yet another expanded illustration of an alternative embodiment of the convoluted annulus-producing lens of the beam-swapping assembly.

In FIG. 6A, another alternative embodiment of 52A of the above-described annulus-generating lens is generated. In this embodiment, the front face of the lens has a slightly curved surface. In FIG. 7B, a further embodiment 52B is illustrated in which the rear face has a complex curved surface. The designs of FIGS. 6A and 6B are useful to generate more complicated ablation profiles. For example, such profiles can be designed by appropriate choice of either the front or rear surface, or both, to compliment any ablation profile that will be subsequently be formed in the eye (or may have already been formed in the eye) as part of the curvature correcting process. In FIG. 6C, a further alternative embodiment 52C is shown in which the flat or truncated cone region on the front face of the lens has been replaced with a hemispherical reflector 59. This hemispherical reflector can be useful to scatter the radiation impinging on the center of the lens in such a way that it can be rapidly absorbed by traps (not shown) in the surrounding support structure.

In sum, the present invention benefits from the recognition that a beam-swapping assembly can be used in conjunction with a beam-shaper to create convoluted ablation patterns of variable depth and, thereby, perform hyperopia and/or astigmatism correcting procedures. The systems and methods of the present invention have several advantages over the prior art. For example, the present invention allows hyperopia correction without the necessity of larger and/or more powerful lasers. The present invention also allows optical correction along with the creation of a blend zone with less waste of energy and an overall shorter procedure time.

It will be understood that the above description pertains to only several embodiments of the present invention. That is, the description is provided by way of illustration and not by way of limitation. For example, many different devices may be used for shaping the beam of ablative radiation, as discussed above. The invention is further characterized according to the following claims.

In the claims:

1. A photorefractive keratectomy system for correction of hyperopia of a cornea of an eye of a patient comprising:
   a radiation source for emitting a beam of ablative radiation;
   an adjustable beam-shaper for receiving the beam and for selectively transmitting at least a portion of the beam along a path to form an exposure pattern on the cornea that varies over time;
   a beam-swapping assembly disposed in the beam path between the beam-shaper and the eye of the patient for modifying the beam that has passed through the beam-shaper into a convoluted annular beam of radiation, and for applying the convoluted annular beam to the cornea to remove a selected volume of corneal tissue from a region in an optical zone of the cornea with the ablative radiation, thereby forming a reprofiled region which steepens at least in part, a curvature of the cornea.

2. The system of claim 1, wherein said beam-shaper comprises a succession of apertures for receiving the beam and for selectively transmitting at least a portion of the beam.

3. The system of claim 1, wherein said beam-shaper comprises at least one mirror of mirrors of different sizes for receiving the beam and for selectively transmitting at least a portion of the beam.

4. The system of claim 1, wherein said beam-shaper comprises a succession of rotating beam modulators for receiving the beam and for selectively transmitting at least a portion of the beam.

5. The system of claim 1, wherein said beam-shaper comprises a succession of graded intensity masks for receiving the beam and for selectively transmitting at least a portion of the beam.

6. The system of claim 1, wherein said beam-shaper comprises a succession of erodable masks for receiving the beam and for selectively transmitting at least a portion of the beam.

7. The system of claim 1, wherein said beam-shaper comprises a cylindrical lens.

8. The system of claim 1, said photorefractive system further comprising a feedback control system for controlling the delivery of pulses of laser energy by measuring a property of said eye.

9. The system of claim 8, wherein said feedback control system comprises a keratometer.

10. The system of claim 1, wherein beam-swapping assembly further comprises a lens element having a front face and a rear face, the front face being conical such that a light beam incident on the front face along an optical axis will be refracted into the convoluted annular beam.

11. The system of claim 10, wherein the front face of the lens element of the beam-swapping assembly has a non-linear surface for varying the intensity profile of the convoluted annular beam.

12. The system of claim 10, wherein the rear face of the lens element of the beam-swapping assembly has a non-linear surface for varying the intensity profile of the convoluted annular beam.

13. The system of claim 10, wherein the front face of said lens element comprises a flat central region.

14. The system of claim 10, wherein the front face of said lens element comprises a reflector element.

15. The system of claim 10, wherein the rear face of said lens element comprises at least one convex region.

16. The system of claim 10, wherein said lens element is aspheric.

17. The system of claim 10, wherein said front face of said lens element comprises a curved surface.

18. The system of claim 10, wherein said rear face of said lens element comprises a curved surface.

* * * * *